(12) United States Patent
Hara et al.

(10) Patent No.: US 12,123,847 B2
(45) Date of Patent: Oct. 22, 2024

(54) ELECTROLYTE ANALYZING DEVICE

(71) Applicant: Hitachi High-Tech Corporation, Tokyo (JP)

(72) Inventors: Masaki Hara, Tokyo (JP); Takushi Miyakawa, Tokyo (JP); Tetsuji Kawahara, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 861 days.

(21) Appl. No.: 17/278,436

(22) PCT Filed: Oct. 25, 2019

(86) PCT No.: PCT/JP2019/041904
§ 371 (c)(1),
(2) Date: Mar. 22, 2021

(87) PCT Pub. No.: WO2020/090652
PCT Pub. Date: May 7, 2020

(65) Prior Publication Data
US 2021/0349052 A1 Nov. 11, 2021

(30) Foreign Application Priority Data
Oct. 31, 2018 (JP) .................... 2018-204877

(51) Int. Cl.
*G01N 27/416* (2006.01)
*G01N 27/30* (2006.01)
(Continued)

(52) U.S. Cl.
CPC ......... *G01N 27/416* (2013.01); *G01N 27/301* (2013.01); *G01N 27/333* (2013.01);
(Continued)

(58) Field of Classification Search
CPC ............. G01N 27/416; G01N 27/4166; G01N 27/301; G01N 27/333;
(Continued)

(56) References Cited

U.S. PATENT DOCUMENTS

| 5,212,992 A | * | 5/1993 | Calhoun | ............... G01F 23/268 |
| | | | | 422/922 |
| 2005/0074363 A1 | * | 4/2005 | Dunfee | .............. G01N 35/1079 |
| | | | | 422/81 |

(Continued)

FOREIGN PATENT DOCUMENTS

| JP | 61-124864 A | 6/1986 |
| JP | 06258277 A * | 9/1994 |

(Continued)

OTHER PUBLICATIONS

Extended European Search Report received in corresponding European Application No. 19879888.6 dated Jun. 27, 2022.

(Continued)

*Primary Examiner* — James Lin
*Assistant Examiner* — Vivian A Tran
(74) *Attorney, Agent, or Firm* — MATTINGLY & MALUR, PC

(57) ABSTRACT

An electrolyte analyzing device with which an electrical effect does not occur has a housing to which a reference potential is applied and a flow passage which is electrically insulated from the housing. The analyzing device delivers a sample solution to a first electrode, and delivers a reference electrode solution to a second electrode. A reagent vessel placement unit which is electrically connected to the housing, has placed thereon a diluent bottle accommodating a diluent, an internal standard solution bottle accommodating the internal standard solution, and a reference electrode solution bottle accommodating the reference electrode solu- (Continued)

tion. The reagent vessel placement unit includes a suction nozzle comprising an electrical conductor which is joined to the flow passage, and which can be inserted into and removed from each of the diluent, internal standard solution and reference electrode solution bottles. And, an insulator electrically insulates the suction nozzle and the housing.

5 Claims, 14 Drawing Sheets

(51) Int. Cl.
  *G01N 27/333* (2006.01)
  *G01N 35/10* (2006.01)
(52) U.S. Cl.
  CPC ..... *G01N 27/4166* (2013.01); *G01N 35/1002* (2013.01); *G01N 35/1011* (2013.01); *G01N 2035/1023* (2013.01)
(58) Field of Classification Search
  CPC ...... G01N 35/10–1002; G01N 35/1009–1011; G01N 35/1032; G01N 2035/1023; G01N 1/38
  See application file for complete search history.

(56) References Cited

U.S. PATENT DOCUMENTS

| 2011/0244557 A1 | 10/2011 | Hamada et al. |
| 2015/0273466 A1* | 10/2015 | Nagai .................... B01L 3/523 422/547 |
| 2019/0265187 A1 | 8/2019 | Kishioka et al. |

FOREIGN PATENT DOCUMENTS

| JP | 09-211007 A | | 8/1997 |
| JP | 2011-209207 A | | 10/2011 |
| JP | 2014142307 A | * | 8/2014 |
| JP | 2015-215274 A | | 12/2015 |
| JP | 2018-4388 A | | 1/2018 |
| WO | 2017/197021 A1 | | 11/2017 |
| WO | 2018/020880 A1 | | 2/2018 |
| WO | 2019/198400 A1 | | 10/2019 |
| WO | 2019/198493 A1 | | 10/2019 |

OTHER PUBLICATIONS

International Search Report of PCT/JP2019/041904 dated Jan. 21, 2020.
Chinese Office Action received in corresponding Chinese Application No. 201980057590.2 dated Jun. 29, 2023.

* cited by examiner

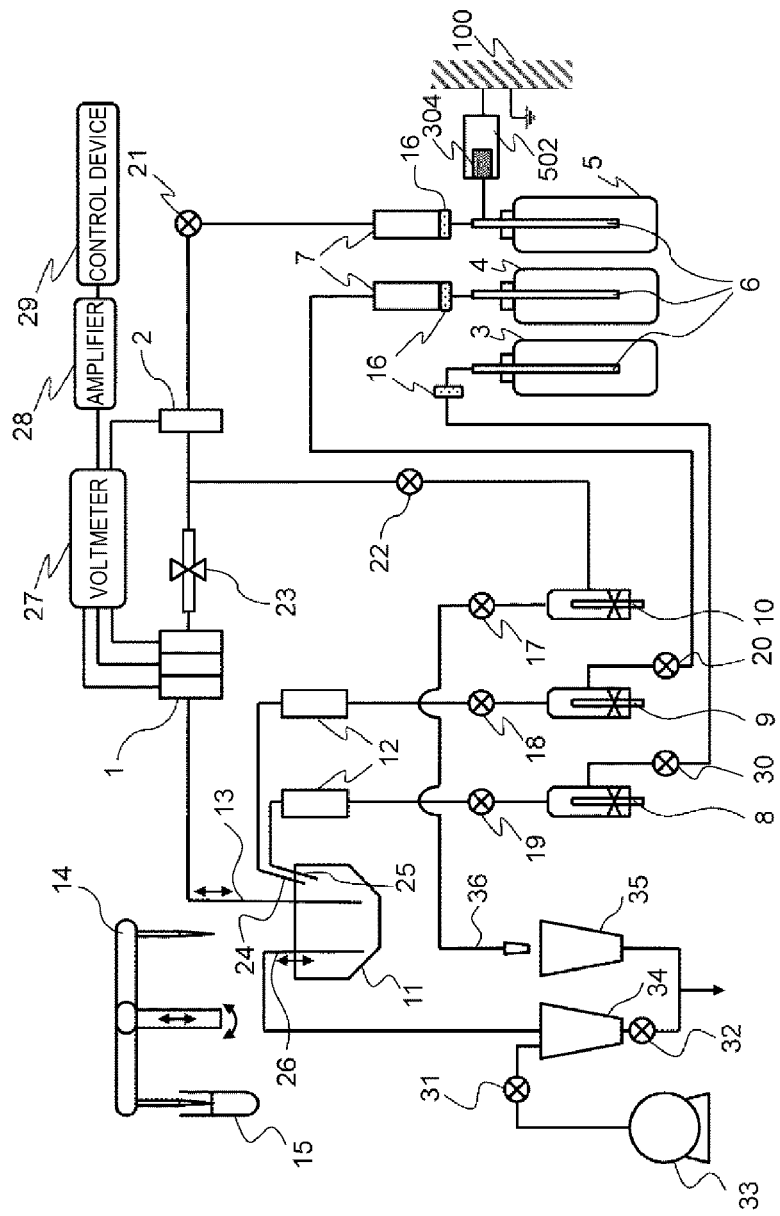
[FIG. 1]

[FIG. 2]
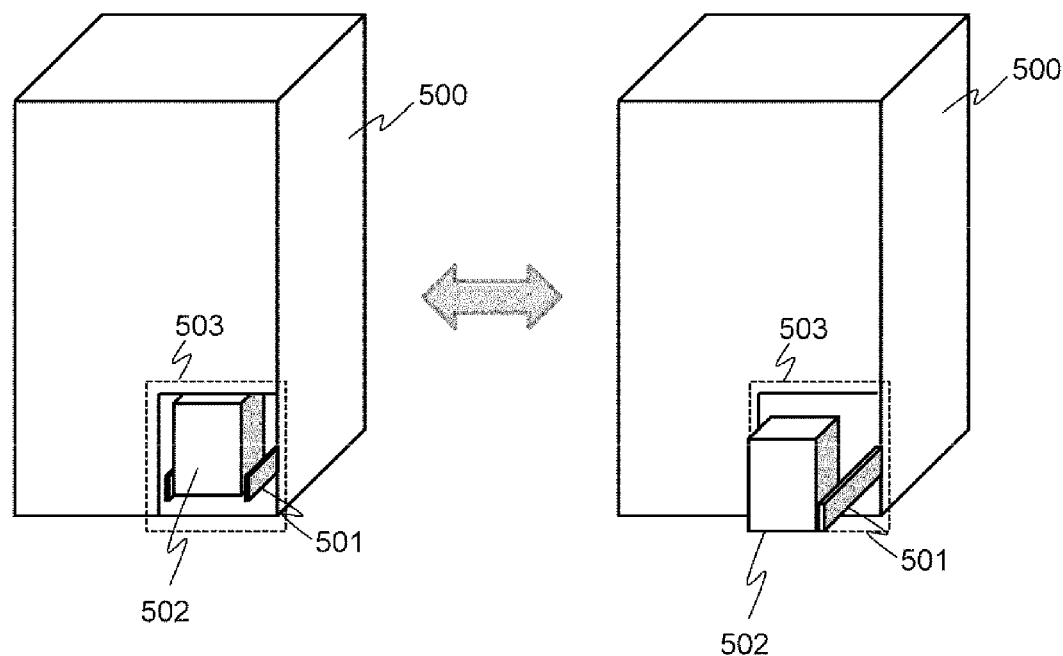

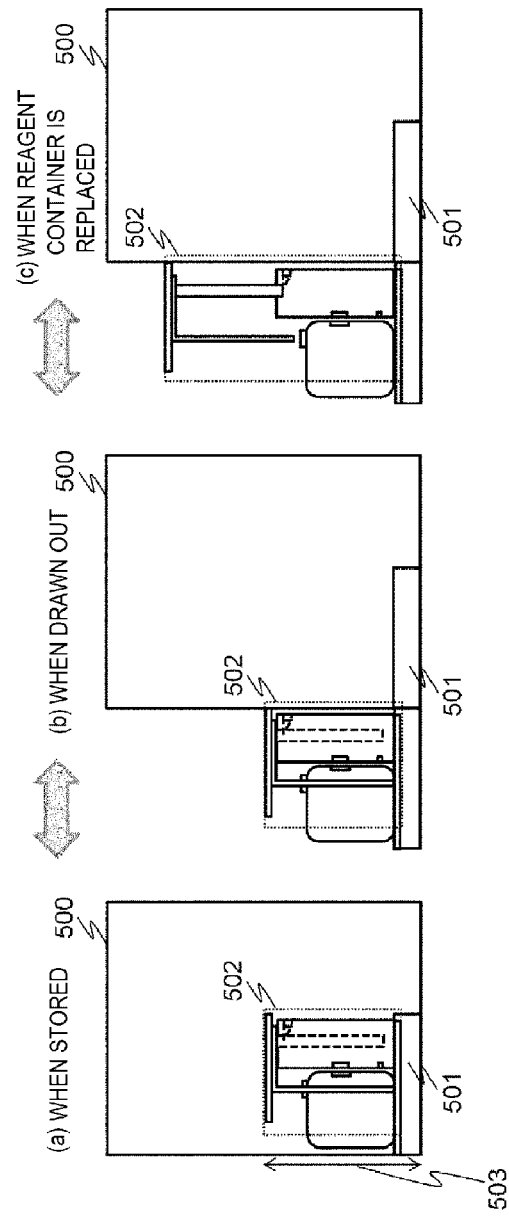

[FIG. 4]
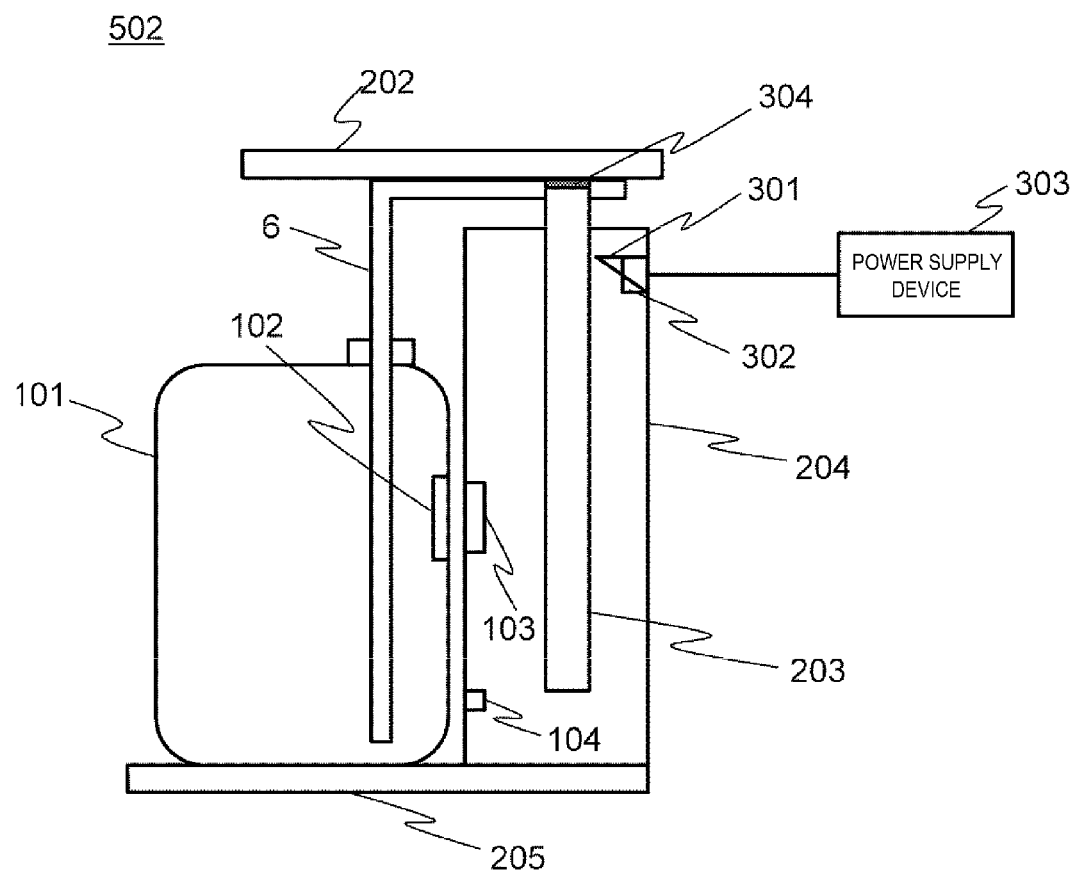

[FIG. 5A]
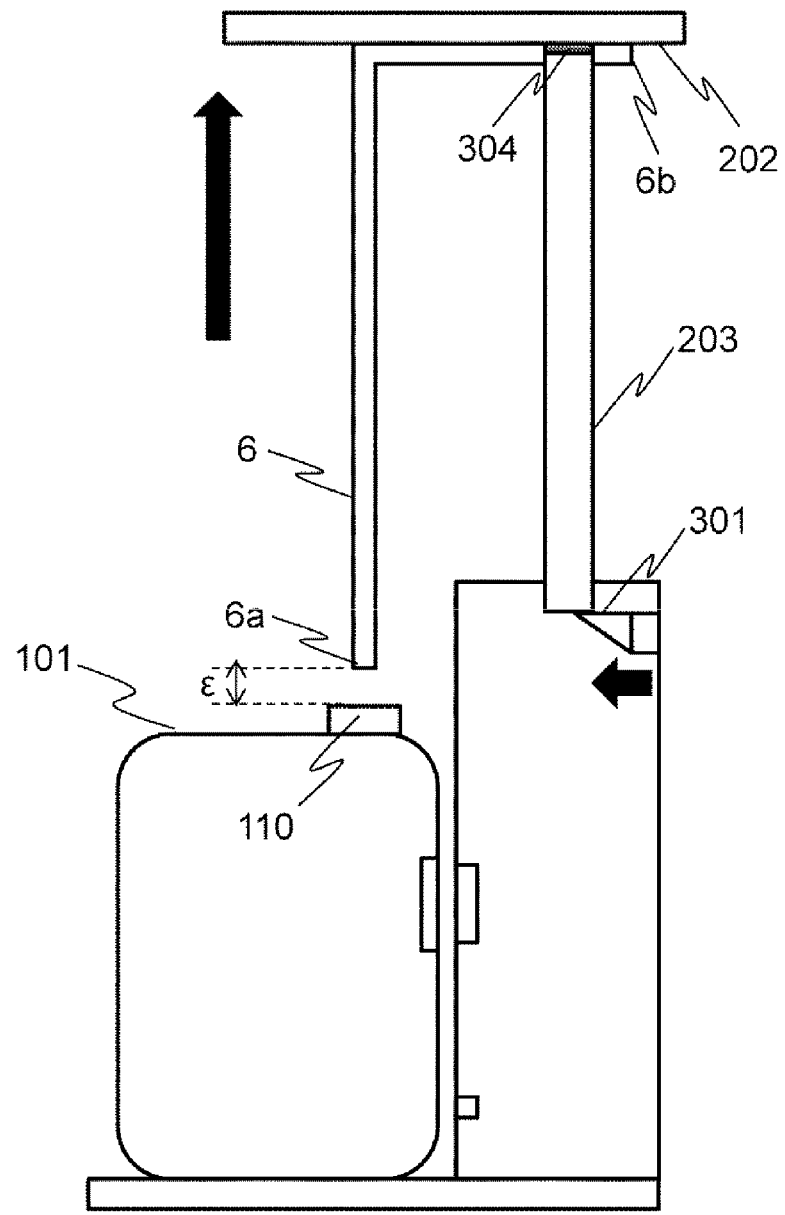

[FIG. 5B]
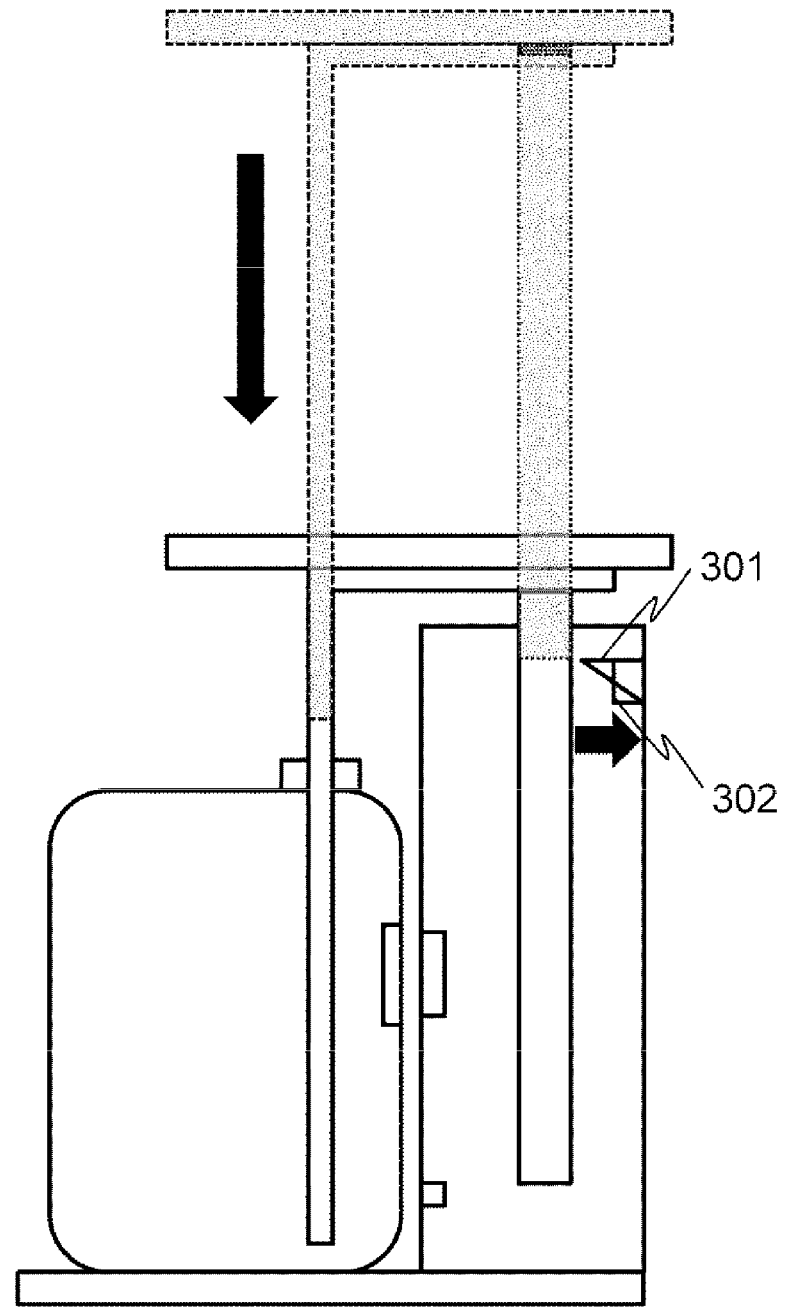

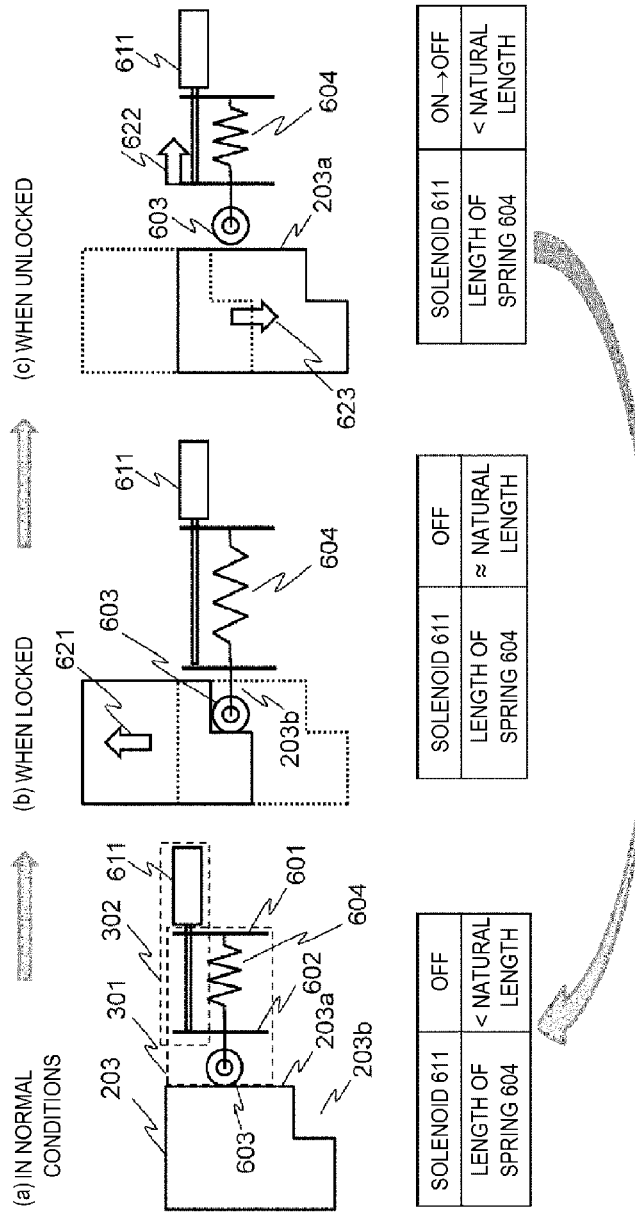
[FIG. 6]

[FIG. 7A]
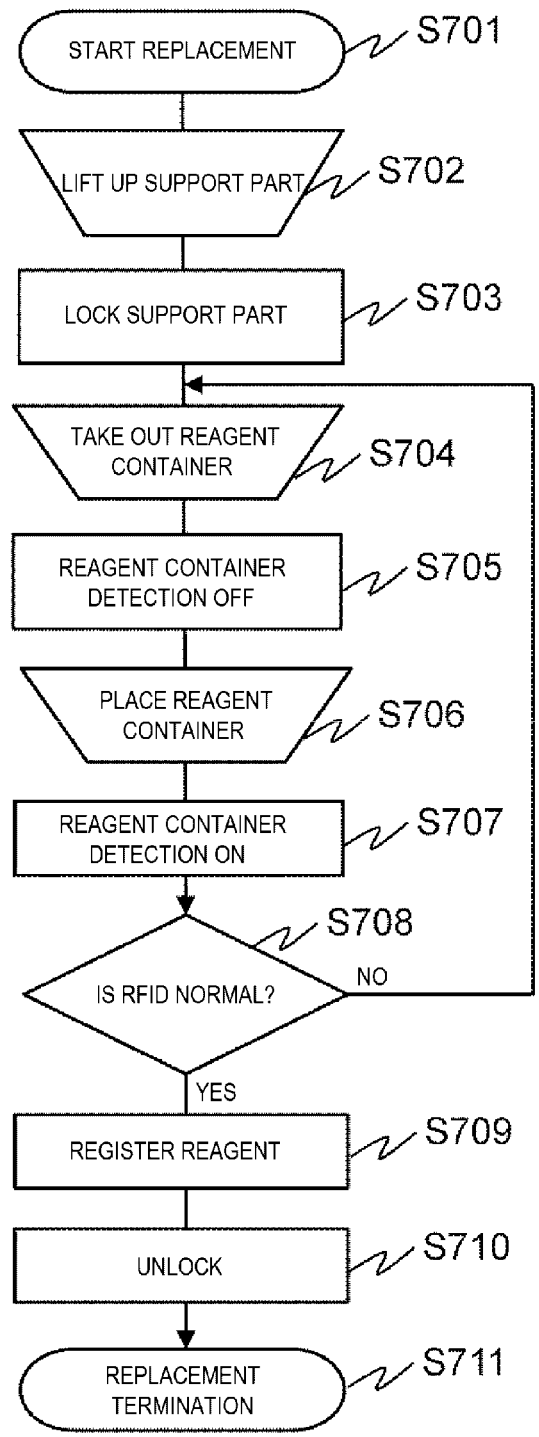

[FIG. 7B]
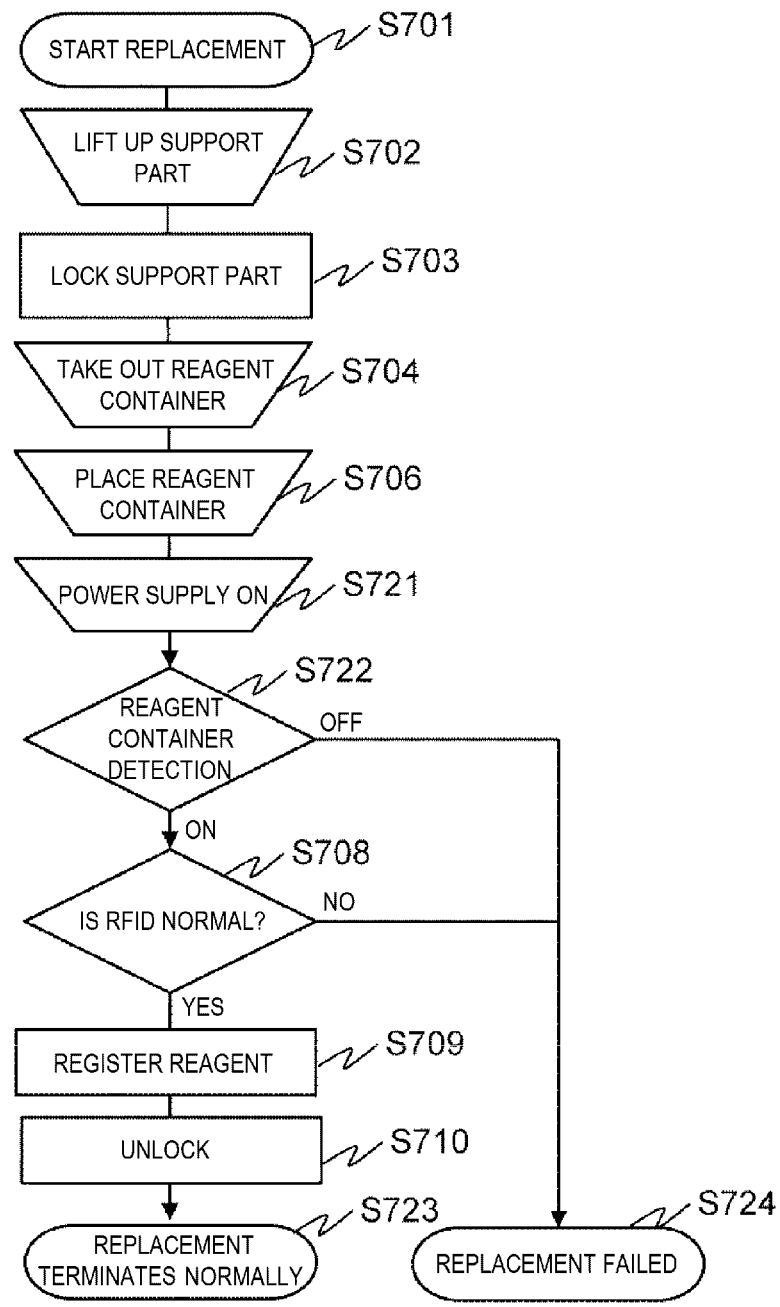

[FIG. 8]
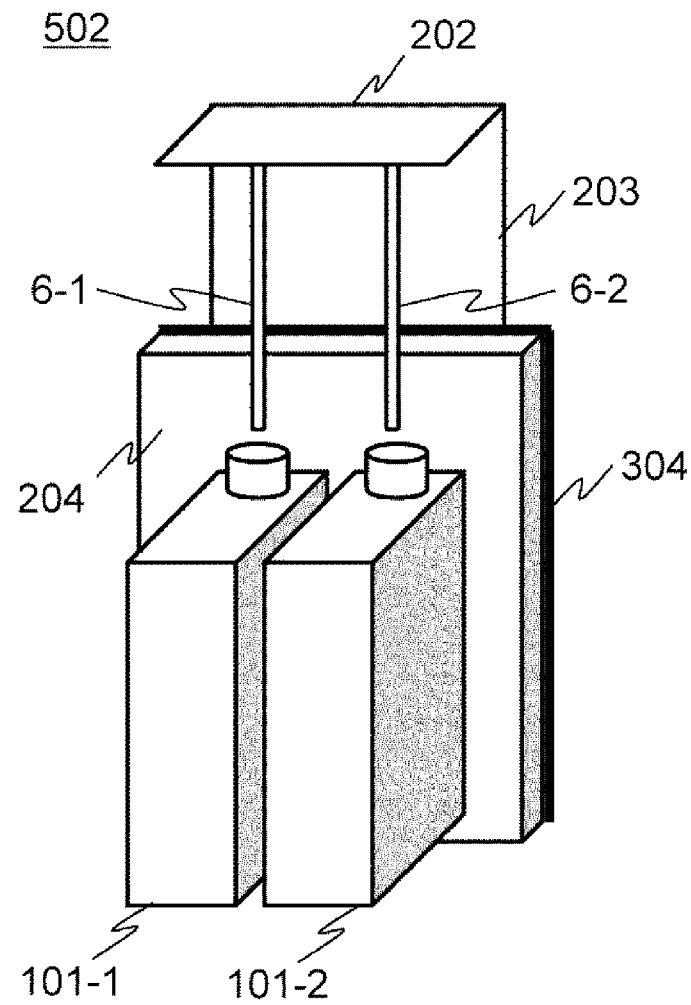

[FIG. 9A]
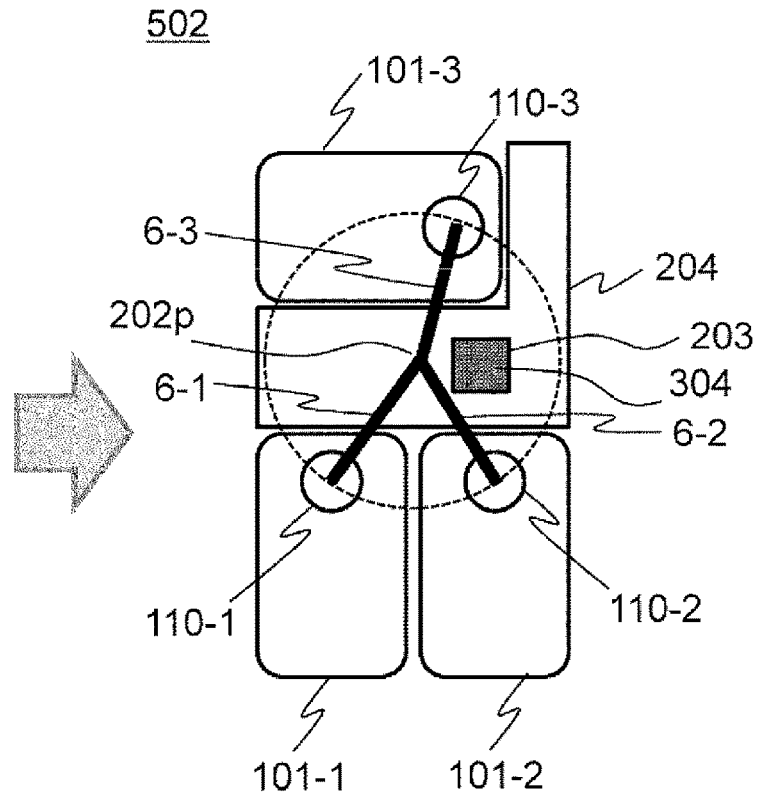
[FIG. 9B]
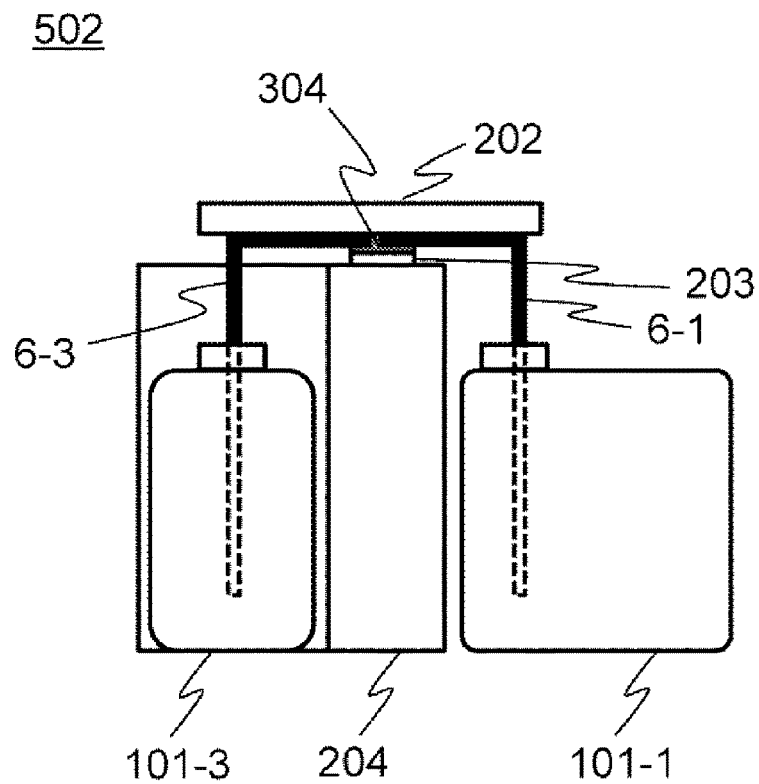

[FIG. 10]
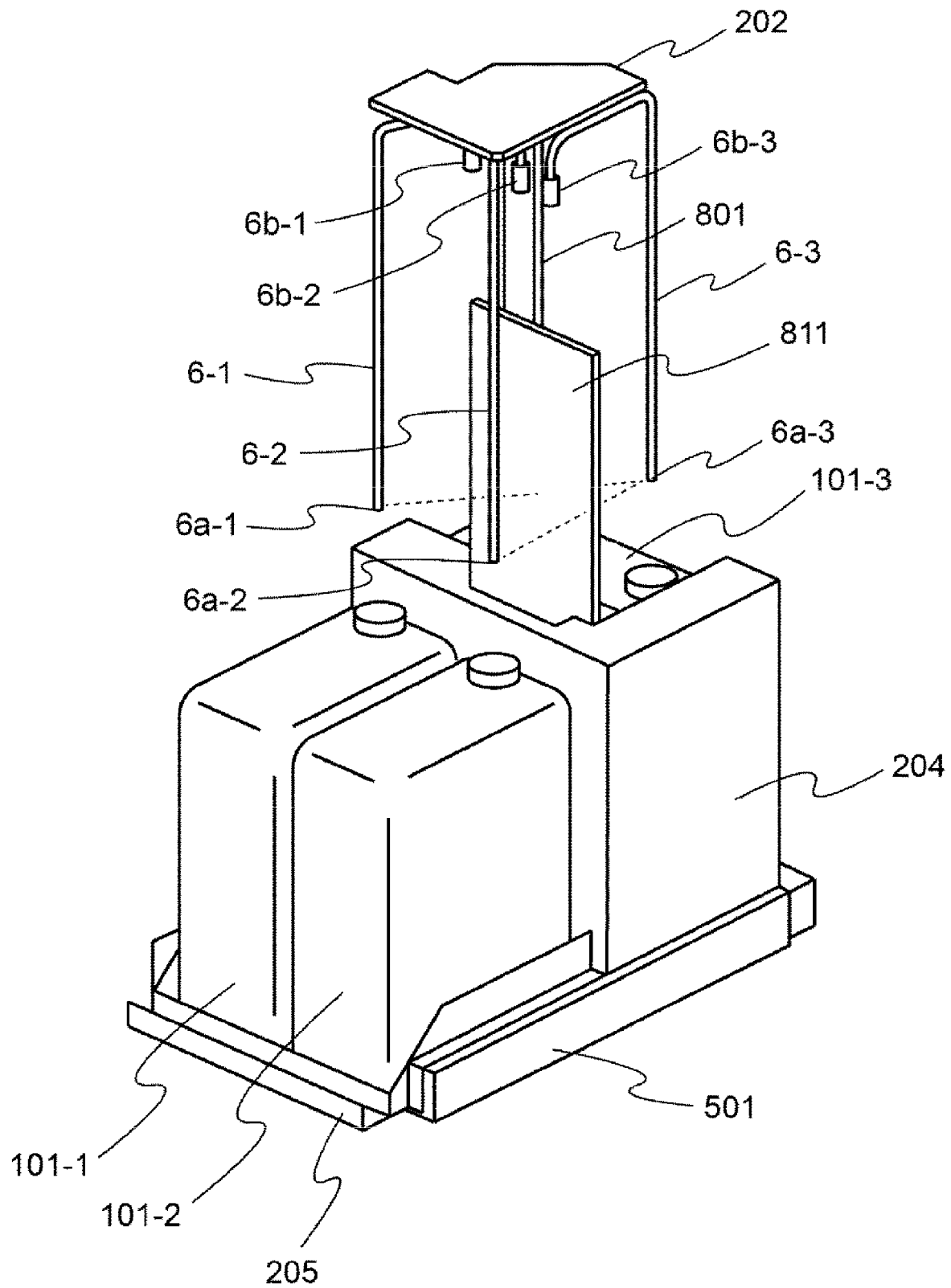

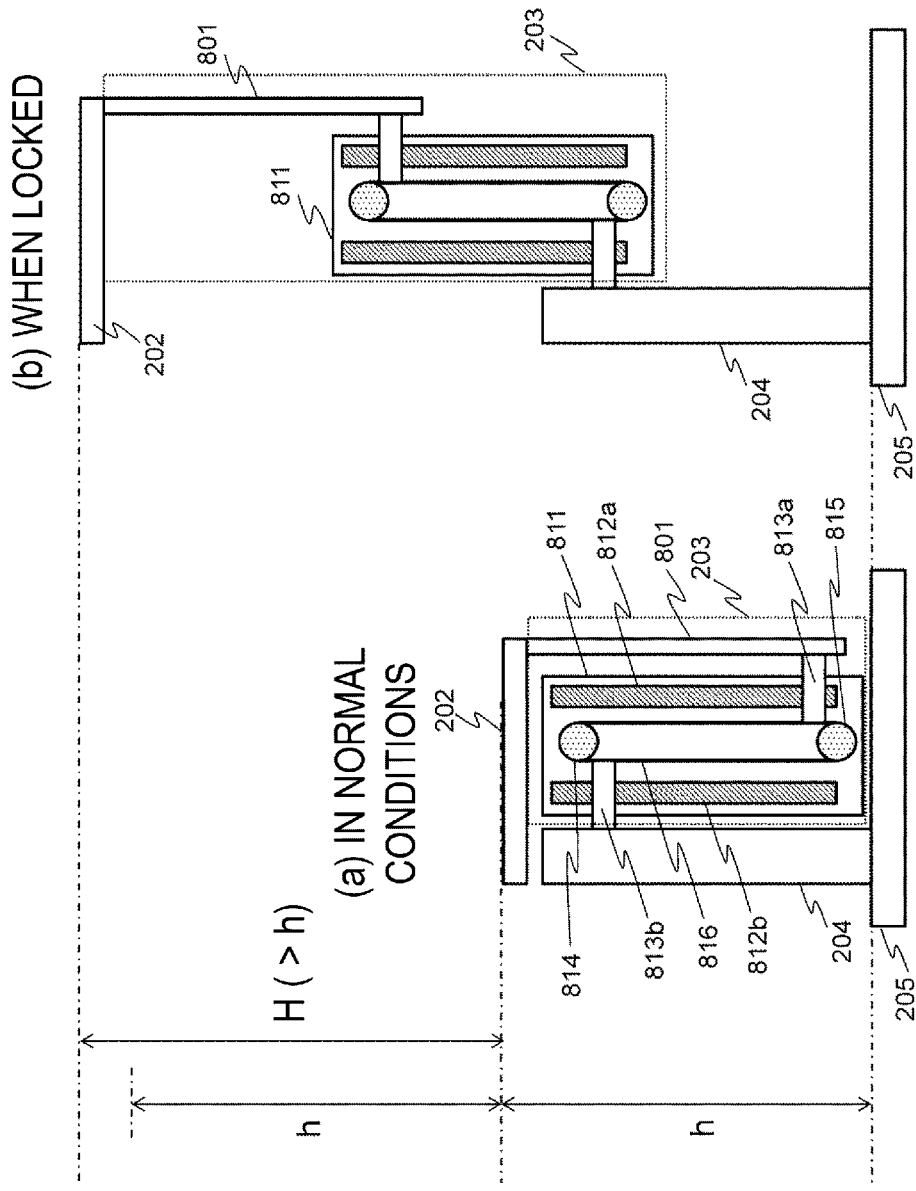

[FIG. 12]
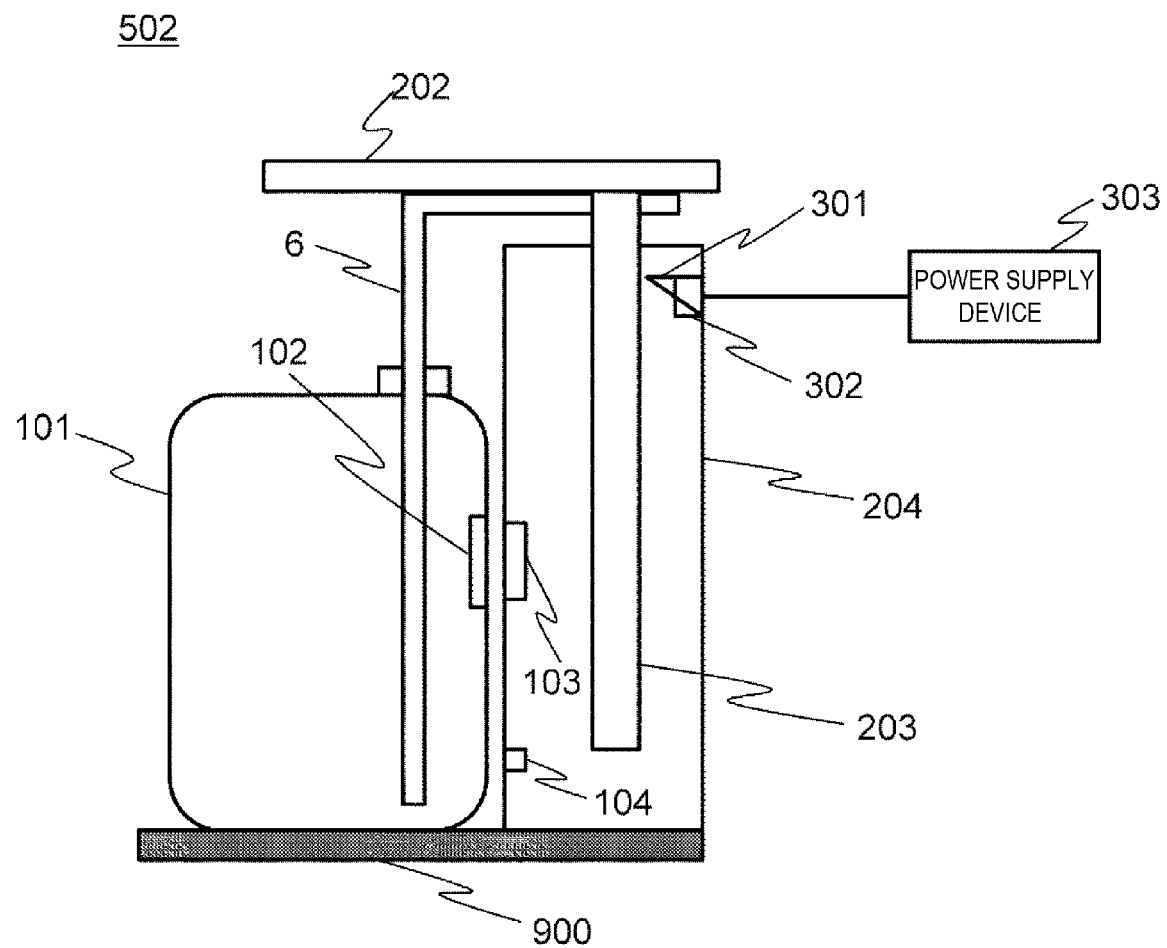

ELECTROLYTE ANALYZING DEVICE

TECHNICAL FIELD

The present invention relates to an electrolyte analysis apparatus.

BACKGROUND ART

The electrolyte analysis apparatus is an apparatus that measures the concentration of a specific electrolyte included in the electrolyte solution such as blood and urine of the human, and the concentration is measured by using an ion selective electrode. As a general measurement method, a sample solution obtained by diluting serum as an electrolyte solution directly or with a diluent is supplied to an ion selective electrode to measure the liquid junction potential of the reference electrode solution, and subsequently (prior to the measurement), the liquid junction potential of the reference electrode solution is measured in the same manner as supplying the standard solution to the ion selective electrode, so that the electrolyte concentration of the sample solution from the two liquid junction potential levels is calculated.

In this manner, in the flow-type electrolyte analysis apparatus, the dilute solution, the standard solution, and the reference electrode solution are used as consumables, and the replacement operation of these reagents is performed by the user. In the flow-type electrolyte analysis apparatus, suction nozzles dedicated to each of these reagents are provided in many cases, while the reagent is mounted on the apparatus, the dedicated suction nozzles and the reagents are generally in a state of being in contact with each other. In the replacement operation by the user, an arrangement of the dedicated suction nozzles into the reagent containers respectively becomes a series of operations.

Since these reagents have different components, due to a mistake made by the user when a reagent container is replaced, if contamination between reagents occurs because different reagents are in contact with a suction nozzle, or the reagent scatters during the replacement operation, there is a problem that a correct measurement result cannot be obtained, a reagent which is a consumable cannot be used, or a flow path of the apparatus is required to be re-cleaned. Particularly, it is desirable that the reference electrode solution is an aqueous solution with a higher concentration than the dilute solution or the standard solution in view of the stability of the analysis by the ion selective electrode, or the measures to prevent contamination with other reagents are indispensable.

JP-A-2011-209207 (PTL 1) discloses that, as a measure for preventing contamination, a sample analysis apparatus includes an information storage medium such as a radio frequency identifier (RFID) attached to a reagent container, and an information reading part that reads the information to an analysis apparatus, so that the sample analysis apparatus has a function of notifying the user of a wrong reagent, a reagent with insufficient remaining amount, and a reagent of which the expiration date is elapsed. Further, in PTL 1, a cover is provided to a container setting unit that sets the reagent container, and a locking mechanism that accepts or prohibits closure of the cover and a control unit thereof are included, to perform the measure for preventing a mistake by the user.

JP-A-H09-211007 (1997) (PTL 2) is provided with a shutter that operates in conjunction with a nozzle, in order to prevent scattering of a sample from a nozzle tip end in a lateral direction, in a dispensing apparatus that dispenses and discharges the sample. A recess part that can insert the nozzle tip end is provided to the shutter, and except for the time other than the suction or the discharge of the sample, the nozzle tip end is inserted to a recess part of the shutter and surrounded, so that the scattering of the sample from the nozzle tip end can be prevented.

CITATION LIST

Patent Literature

PTL 1: JP-A-2011-209207
PTL 2: JP-A-H09-211007 (1997)

SUMMARY OF INVENTION

Technical Problem

In the sample analysis apparatus of PTL 1, in order to prevent misplacement, it is required to supply the power to the sample analysis apparatus. In the configuration of PTL 1, by applying an electric current to a solenoid of a reagent container setting unit, the cover of the reagent container setting unit is controlled to be locked in a closed state or an open state, to prevent the misplacement of the reagent container. Meanwhile, in a state in which an electric current is not applied to the solenoid, the cover of the reagent container setting unit is in an unlocked state. Therefore, in a state in which power is not supplied to the sample analysis apparatus, without performing locking control of the cover by the control unit, the user opens and closes the cover of the reagent container setting unit, so that the replacement operation of the reagent container can be performed.

If the reagent container can be replaced during the time when the analysis apparatus is not in operation, the measurement is not required to be interrupted, and there is an advantage that the operating rate of the analysis apparatus can be increased. Meanwhile, even if the analysis apparatus manages the reagent information with an RFID, in a state in which the power is not supplied to the apparatus, each mechanism cannot be controlled. Therefore, if a suction nozzle comes into contact with another reagent due to a mistake by a human or the like, a contamination risk as described above occurs. Therefore, in a state in which the power is not supplied to the analysis apparatus, the reagent replacement operation is not caused to be completely impossible, but it is desirable that, a portion of the replacement operation, specifically, operations until the suction nozzle is brought into contact with the reagent are able to be performed in a state in which the power is not supplied to the apparatus.

In the case of the dispensing nozzle disclosed in PTL 2, it is required to strictly manage the contamination risk. In contrast, in the case of a nozzle that suctions a reagent according to the present embodiment, a contamination risk differs depending on the type of the reagent. In the case of the electrolyte analysis apparatus targeted in the present embodiment, the influence on a measurement result by the mixture of a small amount of the reagent accompanied by the scattering from the nozzle depends on reagents. Specifically, as described above, the reference electrode solution with a higher concentration has great influence on a measurement result due to the mixture to other reagents, and thus more strict management of a contamination risk is required. However, the dilute solution and the internal standard solution with comparatively lower concentrations have lower contamination risks. Therefore, it is desirable to configure the reagent container setting with a simple mechanism corresponding to the contamination risk.

However, in a case of the electrolyte measurement apparatus, it is required to insulate a flow path from the surroundings according to the measuring principle thereof. In the case of the flow-type electrolyte analysis apparatus, the suction nozzle that suctions the reagent from the reagent container is only introduced into the reagent container to be coupled to the flow path for the measurement. Therefore, if the suction nozzle is a conductor such as metal, it is concerned that electrical noise from the apparatus propagates to the flow path via the suction nozzle, and if the flow path receives such an electrical effect, the measurement accuracy deteriorates.

An object of the present invention is to provide an electrolyte analysis apparatus that suppresses an electrical effect to the measurement by insulating a flow path, even if a suction nozzle is a conductor.

Solution to Problem

According to an aspect of the present invention, an electrolyte analysis apparatus includes a housing that provides a reference electric potential for measurement of the liquid junction potential; a first electrode; a second electrode; a flow path that is electrically insulated from the housing, feeds the sample solution or the internal standard solution to the first electrode, and feeds the reference electrode solution to the second electrode; and a reagent container setting unit that is electrically connected to the housing and sets a dilute solution bottle which houses the dilute solution, an internal standard solution bottle which houses the internal standard solution, and a reference electrode solution bottle which houses the reference electrode solution, in which the reagent container setting unit includes: suction nozzles serving as conductors that are coupled to the flow path and are respectively inserted into or removed from the dilute solution bottle, the internal standard solution bottle, and the reference electrode solution bottle; and an insulator that electrically insulates the suction nozzles from the housing.

Other issues and novel characteristics become apparent from the description of the present specification and accompanying drawings.

Advantageous Effects of Invention

Even if a suction nozzle as a conductor is used, an electrical effect does not occur in an analysis result.

BRIEF DESCRIPTION OF DRAWINGS

FIG. 1 shows an overall schematic diagram of an electrolyte analysis apparatus.

FIG. 2 illustrates an appearance of the electrolyte analysis apparatus (schematic view).

FIGS. 3(a), 3(b) and 3(c) illustrate states of a reagent container setting unit when a reagent container is replaced.

FIG. 4 illustrates a first configuration example of the reagent container setting unit.

FIG. 5A illustrates a state in which a nozzle support part is locked by a locking mechanism.

FIG. 5B illustrates a state in which the nozzle support part is unlocked by an unlocking mechanism.

FIGS. 6(a), 6(b) and 6(c) show configuration examples of the locking mechanism and the unlocking mechanism.

FIG. 7A shows an example of a reagent container replacement flow in an apparatus power-on state.

FIG. 7B shows an example of a reagent container replacement flow in an apparatus power-cutoff state.

FIG. 8 illustrates a second configuration example of a reagent container setting unit.

FIG. 9A illustrates a third configuration example of a reagent container setting unit (plan view).

FIG. 9B illustrates the third configuration example of the reagent container setting unit (side view).

FIG. 10 illustrates a fourth configuration example of a reagent container setting unit (top view).

FIG. 11 illustrates a configuration example of a nozzle support part in the fourth configuration example of the reagent container setting unit.

FIG. 12 illustrates a modification of a reagent container setting unit.

DESCRIPTION OF EMBODIMENTS

FIG. 1 shows an overall schematic diagram of an electrolyte analysis apparatus. The electrolyte analysis apparatus is not limited to a single apparatus and may be mounted on an automatic analysis apparatus. Examples of the automatic analysis apparatus include an automatic biochemical analyzer and an automatic immunity analyzer. Another examples include a mass analysis apparatus used in clinical inspection, a coagulation analysis apparatus that measures coagulation time of the blood, a combined system of the automatic biochemical analyzer and the automatic immunity analyzer with these, and also those mounted on the automatic analysis system obtained by applying these.

The electrolyte analysis apparatus illustrated in FIG. 1 is a flow-type electrolyte analysis apparatus using an ion selective electrode (hereinafter, referred to as an ion selective electrode (ISE electrode)). FIG. 1 illustrates five mechanisms of a sample dispensing part, an ISE electrode part, a reagent part, a mechanism part, and a waste solution mechanism, as the main mechanisms of the electrolyte analysis apparatus, and also illustrates a control device that controls these and calculates and displays the electrolyte concentration from measurement results.

The sample dispensing part includes a sample probe 14. With the sample probe 14, a sample such as a patient sample held in a sample container 15 is dispensed and introduced into the analysis apparatus. Here, the sample is a general term for an analysis target collected from a patient's living body and is, for example, blood or urine. An analysis target that has undergone a predetermined pretreatment on these is also called a sample.

The ISE electrode part includes a dilution tank 11, a sipper nozzle 13, a dilute solution nozzle 24, an internal standard solution nozzle 25, an ISE electrode 1, a reference electrode 2, a pinch valve 23, a voltmeter 27, and an amplifier 28. The sample dispensed in the sample dispensing part is discharged to the dilution tank 11 and diluted and stirred with the dilute solution discharged from the dilute solution nozzle 24 into the dilution tank 11. The sipper nozzle 13 is connected to the ISE electrode 1 by the flow path, and the diluted sample solution suctioned from the dilution tank 11 is fed to the ISE electrode 1 by the flow path. Meanwhile, the reference electrode solution housed in a reference electrode solution bottle 5 is fed to the reference electrode 2 by operating a sipper syringe 10 in a state in which the pinch valve 23 is closed. The diluted sample solution fed to the ISE electrode flow path and the reference electrode solution fed to the reference electrode flow path are in contact with each other, to cause the ISE electrode 1 and the reference electrode 2 to be electrically conductive. The ISE electrode part measures the concentration of the specific electrolyte included in the sample by the potential difference between the ISE electrode 1 and the reference electrode 2.

Specifically, an ion-sensitive film having properties of changing the electromotive force according to the concentration of specific ions (for example, sodium ion ($Na^+$), potassium ion ($K^+$), or chloride ion ($Cl^-$)) in the sample solution can be attached to the ISE electrode 1, and thus the ISE electrode 1 outputs the electromotive force according to each ion concentration in the sample solution and obtains the electromotive force between the ISE electrode 1 and the reference electrode 2 by the voltmeter 27 and the amplifier 28. With respect to each ion, a control device 29 calculates and displays the ion concentration in the sample from the obtained electromotive force. The sample solution remaining in the dilution tank 11 is discharged by the waste solution mechanism.

The potential difference between the ISE electrode 1 and the reference electrode 2 receives the influence of the temperature change. In order to correct the potential fluctuation by the influence of temperature change or the like, the internal standard solution is discharged into the dilution tank 11 by the internal standard solution nozzle 25 between the measurement of one sample and the measurement of the next sample, and the measurement is performed in the same manner as in the case of the above sample (however, the internal standard solution is not diluted). It is preferable to perform correction according to a fluctuation amount by using the result of the internal standard solution measurement performed during the sample measurement.

The reagent part includes a suction nozzle 6 (first suction nozzle, second suction nozzle, third suction nozzle) that suctions the reagent from the reagent container, a degassing mechanism 7, and a filter 16, and supplies the reagent necessary for the measurement. In the case of the electrolyte measurement, three kinds of reagents of the internal standard solution, the dilute solution, and the reference electrode solution are used as the reagents, and an internal standard solution bottle 3 that houses the internal standard solution, a dilute solution bottle 4 that houses the dilute solution, and the reference electrode solution bottle 5 that houses the reference electrode solution are set in the reagent part. FIG. 1 illustrates the state. In the case of cleaning the apparatus, a cleaning liquid bottle that stores cleaning liquid is set in the reagent part.

The internal standard solution bottle 3 and the dilute solution bottle 4 are connected to the internal standard solution nozzle 25 and the dilute solution nozzle 24 through the flow paths via the filters 16, respectively. Each nozzle is set in a shape in which the tip end is introduced into the dilution tank 11. The reference electrode solution bottle 5 is connected to the reference electrode 2 through the flow path via the filter 16. Each degassing mechanism 7 is connected to the flow path between the dilute solution bottle 4 and the dilution tank 11 and the flow path between the reference electrode solution bottle 5 and the reference electrode 2. The degassed reagent is supplied to the inside of the dilution tank 11 and the inside of the reference electrode 2. This is because the flow path is negatively pressured by the syringe and the reagent is suctioned up from the bottle, so that the gas dissolved in the reagent appears as bubbles in the reagent. The degassing mechanism is provided so that the reagent is not supplied to the dilution tank 11 or the reference electrode 2 with bubbles contained therein.

The mechanism part includes an internal standard solution syringe 8, a dilute solution syringe 9, the sipper syringe 10, electromagnetic valves 17, 18, 19, 20, 21, 22, 30, and a preheat 12, and performs an operation of feeding liquid into each mechanism or between mechanisms. For example, the internal standard solution and the dilute solution are fed to the dilution tank 11 by the operations of the internal standard solution syringe 8, the dilute solution syringe 9, and the electromagnetic valves provided to the flow paths. The preheat 12 controls the temperatures of the internal standard solution and the dilute solution reaching the ISE electrode 1 within a certain range to suppress the influence of the temperature on the ISE electrode 1.

The waste solution mechanism includes a first waste solution nozzle 26, a second waste solution nozzle 36, a vacuum bottle 34, a waste solution receiver 35, a vacuum pump 33, and electromagnetic valves 31 and 32, and discharges the sample solution remaining in the dilution tank 11 and a reaction solution remaining in the flow path of the ISE electrode part.

The electrolyte concentration measurement operation by the electrolyte measurement apparatus illustrated in FIG. 1 is described. The measurement operation is controlled by the control device 29.

First, the sample dispensed from the sample container 15 by the sample probe 14 of the sample dispensing part is discharged to the dilution tank 11 of the ISE electrode part. After the sample is dispensed to the dilution tank 11, the dilute solution is discharged from the dilute solution bottle 4 through the dilute solution nozzle 24 by the operation of the dilute solution syringe 9 and dilutes the sample. As described above, in order to prevent the bubbles from occurring due to changes in the temperature or the pressure of the dilute solution in the flow path, the degassing process is performed by the degassing mechanism 7 installed in the middle of the dilute solution flow path. The diluted sample solution is suctioned to the ISE electrode 1 by the operations of the sipper syringe 10 or the electromagnetic valve 22.

Meanwhile, the reference electrode solution is fed from the reference electrode solution bottle 5 into the reference electrode 2 by the pinch valve 23 and the sipper syringe 10. The reference electrode solution is, for example, an aqueous solution of potassium chloride (KCl) with a predetermined concentration, and the sample solution and the reference electrode solution are in contact with each other, to cause the ISE electrode 1 and the reference electrode 2 to be electrically conductive. The electrolyte concentration of the reference electrode solution suppresses the influence of the concentration fluctuation during the sample feeding, and thus the high concentration is desirable. However, it is likely that the electrolyte crystallizes near the saturation concentration to cause channel clogging, and thus the electrolyte concentration is desirably 0.5 mmol/L to 3.0 mmol/L. The ISE electrode potential based on the reference electrode potential is measured by using the voltmeter 27 and the amplifier 28.

The internal standard solution of the internal standard solution bottle 3 set in the reagent part before and after the sample measurement is discharged to the dilution tank 11 by the internal standard solution syringe 8, and the electrolyte concentration of the internal standard solution is measured in the same manner as the sample measurement.

The electrolyte concentration in the sample is calculated with the control device 29 by using the ISE electrode potential measured with respect to the sample solution. In this case, the electrolyte concentration can be more accurately measured by the correction based on the ISE electrode potential measured with respect to the internal standard solution.

In such an electrolyte measurement apparatus, the flow path through which the reagent is supplied and that is formed with the ISE electrode part, the reagent part, and the mechanism part has weak potential. In order to measure the electrolyte with high accuracy, the flow path needs to be insulated from the surrounding environment and not to receive the electrical effect. Examples of the method thereof include forming the flow path that is in contact with the reagent or the sample solution with an insulator such as a resin. However, it is required that the suction nozzle 6 is inserted into or removed from the reagent bottle, and thus the suction nozzle 6 coupled to the flow path may be desired to be formed with a conductor such as metal, as described below.

Here, in the housing of the electrolyte measurement apparatus, a power supply for driving each mechanism and AC wiring for supplying an electric power from the power supply are provided, and also a housing 100 is a reference electric potential (GND) to be measured by the electrolyte measurement apparatus. Therefore, when the suction nozzle 6 is a conductor, the suction nozzle 6 generates a state of being electrically connected to the housing 100 via a reagent container setting unit 502 which is a mechanism on the housing side. In this case, the potential of the flow path escapes to the housing 100, or a weak noise is locally applied to the housing 100 if a power supply or AC wiring is provided to a portion near the reagent container setting unit 502, and thus it is concerned that the potential of the flow path may fluctuate. Therefore, according to the present embodiment, as illustrated in FIG. 1, in order to prevent the suction nozzle 6 which is a conductor from being electrically connected to the housing 100, an insulator 304 is provided to the reagent container setting unit 502. In the drawings, only the suction nozzle 6 inserted to the reference electrode solution bottle 5 is illustrated, but the same is applied to the suction nozzles 6 that are inserted into the other reagent bottles.

In addition, the control device can be configured as a computer including a central processing unit (CPU), a random access memory (RAM), a storage device, and an I/O port, and the RAM, the storage device, and the I/O port are configured to exchange data with the CPU via an internal bus. The I/O port is connected to each mechanism described above, and controls these operations. The operation is controlled by reading the program stored in the storage device into the RAM and executing the program by the CPU. In addition, an input and output device is connected to the control device 29, so that the input from the user or the measurement result can be displayed.

Subsequently, the reagent container setting unit of the electrolyte analysis apparatus according to the present embodiment is described. FIG. 2 illustrates an appearance of the electrolyte analysis apparatus (schematic view). The reagent container setting unit 502 in which the internal standard solution bottle 3, the dilute solution bottle 4, and the reference electrode solution bottle 5 are set can be drawn from a housing 500 of the apparatus through an opening 503 with a rail 501. The opening 503 is generally closed by a door (not illustrated), and the door is opened when a reagent container is replaced so that the reagent container is replaced. When a reagent container is replaced, as illustrated in FIG. 2 (right figure), the entire reagent container setting unit 502 is drawn to the outside of the housing 500 so that the user can easily replace the reagent container. After the reagent container replacement operation, the reagent container setting unit 502 is stored in the housing 500 again (FIG. 2 (left figure)).

FIGS. 3(a), 3(b) and 3(c) illustrate states of the reagent container setting unit when the reagent container is replaced. FIG. 3(a) illustrates the time when the reagent container setting unit 502 is stored, FIG. 3(b) illustrates the time when the reagent container setting unit 502 is drawn, FIG. 3(c) illustrates the time when the reagent container is replaced, and all are perspective views from the side surface of the housing 500. A configuration example of the reagent container setting unit 502 is described below.

Embodiment 1

FIG. 4 illustrates a first configuration example of the reagent container setting unit 502. The figure illustrates a cross-sectional view (schematic view) in a state where the suction nozzle 6 of the reagent container setting unit 502 is inserted into a reagent container 101. In the reagent container setting unit 502, a reagent container stand 204 is provided on a substrate 205. The reagent container 101 is placed on the substrate 205, and simultaneously the substrate 205 is coupled to the rail 501 (not illustrated) so that the reagent container setting unit 502 can be taken into and out of the housing of the apparatus. The suction nozzle 6 is coupled to a nozzle support part 203 that can be raised and lowered from and to the reagent container stand 204 via a handle 202 and the insulator 304.

FIG. 5A illustrates a state in which the nozzle support part 203 is locked by a locking mechanism 301. When the user replaces the reagent container 101, the user manually pulls up the handle 202, so that the suction nozzle 6 can be separated from the reagent container 101 without touching the suction nozzle 6. If the nozzle support part 203 is lifted to the upper limit point, the nozzle support part 203 is held by the locking mechanism 301 at the position as illustrated in FIG. 5A. This position is referred to as a reagent container replacement position. Accordingly, this allows the user to release the handle 202 and perform the replacement operation of the reagent container 101.

The suction nozzle 6 is configured with a metal pipe fixed so that the nozzle tip end position is not deviated from the position where the reagent container 101 is placed when a user pulls up the handle 202. Accordingly, it is possible to prevent the reagent from scattering to the surroundings due to the deflection of a suction nozzle tip end 6a according to the operation that is assumed when the suction nozzle 6 is made of a flexible resin pipe. Meanwhile, an end portion 6b on the handle side of the suction nozzle 6 is connected to a pipe (not illustrated), and the suction nozzle 6 is connected to the flow path of the apparatus. By using a flexible resin pipe for the pipe connected to a suction nozzle end portion 6b, it is possible to make it easy to put the reagent container setting unit 502 in and out of the housing and to raise and lower the nozzle support part 203.

In this manner, the reagent container setting unit 502 has a movable part and is required to have a certain strength, and thus metal is used in a lot of portions thereof due to the ease of processing. For example, the handle 202, the nozzle support part 203, the reagent container stand 204, and the substrate 205 are parts that have many merits of being formed of metal because of the above advantages. Therefore, when the suction nozzle 6 is configured with a metal pipe, as described above, the suction nozzle 6 fixed to the handle 202 is electrically connected to the housing via the nozzle support part 203, the reagent container stand 204, and the substrate 205 and is likely to cause fluctuations in the potential of the flow path. Therefore, as illustrated in FIG. 4, the insulator 304 is arranged between the handle 202 and the nozzle support part 203. In addition, the suction nozzle 6 is fixed to the handle 202, and is not in contact with any portion of the reagent container setting unit 502 other than the handle 202. As a result, the suction nozzle 6 and the handle 202 can be in a state of being insulated from the apparatus.

In a state where the nozzle support part 203 is locked by the locking mechanism 301, it is desirable that a predetermined distance ε is provided between the suction nozzle tip end 6a and a reagent suction port 110 of the reagent container 101 (FIG. 5A). According to this, the user does not hit the reagent container 101 with the suction nozzle tip end 6a or does not need to tilt and place the reagent container on the reagent container setting unit when replacing the reagent container 101. Therefore, it is possible to suppress the risk of occurrence of the spillover of the reagent from the reagent container 101 during the replacement or the scattering of the reagent from the suction nozzle tip end 6a.

FIG. 5B illustrates a state in which the nozzle support part 203 is unlocked by an unlocking mechanism 302 from the state illustrated in FIG. 5A. The locking mechanism 301 performs unlocking according to the control of the control device 29 by the unlocking mechanism 302 in a state in which the power is supplied from a power supply device 303 to an unlocking mechanism 302. At this time, it is desirable that a damper mechanism is provided to the nozzle support part 203 so that the suction nozzle 6 and the nozzle support part 203 are slowly lowered, even if the user does not grip the handle 202. In the present example, the nozzle support part 203 is stopped in a fully lowered state, and the position is referred to as a reagent suction position.

FIGS. 6(a), 6(b) and 6(c) show configuration examples of the locking mechanism 301 and the unlocking mechanism 302. The locking mechanism 301 includes a base on fixed side 601 and a base on movable side 602, and a spring 604 is provided between the base on fixed side 601 and the base on movable side 602. In addition, a bearing 603 is connected to the surface of the base on movable side 602 facing the surface on which the spring 604 is provided. The unlocking mechanism 302 has a solenoid 611, and the solenoid 611 is connected to the base on movable side 602.

(a) The reagent container setting unit 502 in normal times is in the state of FIG. 4. In normal times, the solenoid 611 is turned off, and the bearing 603 is in contact with a guide part 203a of the nozzle support part 203. At this time, the spring 604 is compressed, and the bearing 603 is pressed against the guide part 203a by the elastic force of the spring 604.

(b) The reagent container setting unit 502 at the locked time is in the state of FIG. 5A. The solenoid 611 is turned off even at the locked time. The nozzle support part 203 is lifted in a direction 621, and the bearing 603 is fitted with a lock recess part 203b provided in the nozzle support part 203. As a result, the nozzle support part 203 is locked so as not to descend even when the user releases the handle. At this time, the length of the spring 604 becomes the length close to the natural length.

In this manner, regardless of whether the power is supplied or not, by using the elastic force of the spring, the nozzle support part 203 can be lifted to draw the suction nozzle 6 from the reagent container 101 and lock the suction nozzle 6 in that state. The present embodiment is not limited to the spring, and an elastic body can be used. As long as electric power is not required for the operation, the nozzle support part 203 may be locked by another mechanical action.

(c) The reagent container setting unit 502 when being unlocked is in the state of FIG. 5B. The solenoid 611 is turned on and attracts the bearing 603 and the base on movable side 602 in a direction 622. As a result, the bearing 603 is pulled out from the lock recess part 203b, and the nozzle support part 203 descends in a direction 623. After a predetermined time, the solenoid 611 is turned off, and the bearing 603 comes into contact with the guide part 203a of the nozzle support part 203. When the nozzle support part 203 fully descends, the nozzle support part 203 returns to the normal state.

In order to operate the solenoid 611, it is required that the electric power is supplied to the solenoid 611, and the control device 29 performs control so that the solenoid 611 is turned on. As a result, in order to unlock the nozzle support part 203 and insert the suction nozzle 6 into the reagent container, the power supply of the apparatus must be supplied. As long as the unlocking operation is controlled by the control device 29, the unlocking mechanism 302 may unlock the nozzle support part 203 by another action. For example, the lock may be released by the air pressure exceeding the elastic force of the spring.

Further, an RFID tag 102 in which information related to the reagent such as the type of the reagent, the remaining liquid amount, the expiration date, and the lot number is stored is attached to the reagent container 101 (see FIG. 4). In order to exchange information with the RFID tag 102, the reagent container stand 204 is provided with an RFID reader-writer 103 at a facing position in a state in which the reagent container 101 is placed. Further, a container detector 104 that detects whether the reagent container 101 is the reagent container is positioned at the reagent container placing position is provided. For example, the container detector 104 includes, for example, a light source that emits infrared light and a photodetector that detects infrared light. The light detector detects whether the reflected light from the reagent container 101 is present to determine whether the reagent container 101 is present. Further, the RFID tag and the RFID reader-writer are examples, and it is preferable that an information storage medium that stores information about the housed reagent is attached to the reagent container, and the information reader installed in the reagent container setting unit reads the information relating to the reagent housed, which is stored in the information storage medium.

Subsequently, a replacement flow of the reagent container is described. As described above, in the reagent container setting unit 502 of the present embodiment, regardless of the supply of the apparatus power, the original reagent container can be removed and a new reagent container can be set. However, the suction nozzle can be inserted into a new reagent container, only in a state in which the apparatus power is supplied. FIG. 7A shows an example of a reagent container replacement flow in an apparatus power-on state, and FIG. 7B shows an example of a reagent container replacement flow in an apparatus power-cutoff state.

First, the reagent container replacement flow in the apparatus power-on state (FIG. 7A) is described. As described above, the user grasps the handle 202 and lifts the nozzle support part 203 (S702). In the state in which the nozzle support part 203 is locked (S703), the reagent container 101 is removed (S704). Accordingly, the reagent container detection by the container detector 104 is turned off (S705). If the new reagent container 101 is again placed to the reagent container setting unit 502 by the user (S706), the container detector 104 detects the new reagent container 101 (S707). The RFID reader-writer 103 is triggered by the detection of the reagent container by the container detector 104 to start reading the RFID information of the reagent container 101. The control device 29 determines whether the RFID information is normal (S708). Examples of the determination content include whether the type of the reagent is a reagent that should be originally placed in the placing location, whether the remaining liquid amount is sufficient, and whether the expiration date of the reagent is not passed. If the RFID information is normal, the control device 29 registers the read RFID information (S709) and performs an unlocking operation of the locking mechanism 301 by the unlocking mechanism 302 (S710). When being unlocked, the nozzle support part 203 automatically descends, and the suction nozzle 6 moves to a predetermined suction position in the reagent container 101. Meanwhile, if the RFID information is not normal, the fact is display at the display portion of the control device 29. Accordingly, the user can replace the reagent container with a right reagent container, before the suction nozzle 6 comes into contact with a wrong reagent. (S704 to S706). In this manner, since the suction nozzle 6 comes into contact only with a normal reagent, it is possible to prevent contamination caused by misplacement of the reagent container by the user.

Subsequently, the reagent container replacement flow in the apparatus power-cutoff state (FIG. 7B) is described. Steps having the same contents as the replacement flow of FIG. 7A are denoted by the same reference numerals. The user grasps the handle 202 and lifts the nozzle support part 203 (S702). In a state in which the nozzle support part 203 is locked (S703), the reagent container 101 can be replaced (S704 and S706). As described above, the locking mechanism 301 of the present embodiment can lock the nozzle support part 203 mechanically without supplying power. If the apparatus power is supplied by the user (S721), the apparatus checks the state of the container detector 104 of the reagent container setting unit 502 as one of the initial process (S722). If the container detector 104 detects the reagent container 101, the detection triggers the checking of the RFID information (S708). If the RFID information is normal, the control device 29 registers the read RFID information (S709) and performs the unlocking operation of the locking mechanism 301 by the unlocking mechanism 302 (S710). Meanwhile, if the reagent container is not detected, or the RFID information is not normal, the replacement is failed (S724), and the fact is displayed on the display portion of the control device 29. In this case, the apparatus power is already supplied, the process proceeds to Steps S704 or S705 of FIG. 7A and performs the replacement process of the reagent. If the replacement is normally completed (S723), the control device 29 thereafter automatically performs a liquid replacement operation in the flow path, an analysis preparation operation, and the like, if necessary.

Generally, the electrolyte analysis apparatus has a function of automatically performing the liquid feeding operation into the flow path, the apparatus status check operation, the cleaning operation, and the like in the initial process after the power is turned on and proceeding to the analysis operation at a short period of time. However, if it is recognized that the remaining amount of the reagent is not sufficient after the initial process, and the reagent container is replaced, a liquid replacement operation in the flow path or the like is required again, and as a result, the time until the start of analysis is required. According to the present embodiment, the user can perform the reagent replacement operation while maintaining the effect of preventing contamination between the reagents even when the device power is turned off, and thus can use the apparatus without performing an additional operation after the power is turned on.

FIG. 12 illustrates a modification of the reagent container setting unit 502. The difference from FIG. 4 is that the substrate 205 is used as an insulation substrate 900, to fulfill the function of the insulator 304 of FIG. 4. By changing the arrangement position of the insulator to the substrate, the entire reagent container setting unit 502 can be caused to be in the insulation state. In this example, there is an advantage that the substrate is insulated, and thus the configuration of the upper part of the substrate is not limited. In this manner, an insulator may be arranged at a position where the electrical connection between the suction nozzle 6 and the housing can be prevented. In the present embodiment, the arrangement position of the insulator 304 is not limited to a specific location. For example, the handle 202 can be configured with an insulator such as a resin. The same is applied to the following embodiment. The plurality of insulators 304 may be arranged between the suction nozzle 6 and the housing.

Further, if the reagent container 101 is a container made of a transparent or translucent material, and the reagent container setting unit 502 is configured to be easily visible to the user, it is convenient because the user can visually check the remaining amount of the reagent before the apparatus power is supplied, and thus reagent can be replaced in advance, if necessary.

Embodiment 2

FIG. 8 illustrates a second configuration example of the reagent container setting unit 502. In a second configuration example, the main difference from the first configuration example is that two suction nozzles 6-1 and 6-2 are coupled to the nozzle support part 203, the handle 202 is lifted by the user, and thus the two suction nozzles 6-1 and 6-2 are simultaneously lifted. In this example, the insulator 304 is provided between the nozzle support part 203 and the reagent container stand 204, and the flow path is insulated by one insulator with respect to two suction nozzles provided to the handle 202. The position where the insulator 304 is provided is not limited to the configuration illustrated in FIG. 8, and may be arranged between the handle 202 and the nozzle support part 203 as in Embodiment 1. In any case, it is not required to provide the insulator for each suction nozzle. Though not illustrated in FIG. 8, the container detector 104 or the RFID reader-writer 103 illustrated in FIG. 4 are provided corresponding to reagent containers 101-1 and 101-2, respectively. The reagent container replacement flow is also as illustrated in FIGS. 7A and 7B. When one or more reagent containers are replaced by the user, and RFID information of the all reagent containers is normal, locking of the nozzle support part 203 is unlocked by the unlocking mechanism 302, such that the suction nozzles 6-1 and 6-2 are moved to the predetermined suction positions in the reagent containers 101-1 and 101-2, respectively. In FIG. 8, an example of two reagent containers is provided, but three or more reagent containers may be provided.

According to the present configuration, the user can simultaneously perform the reagent container replacement operation by the required amount by one time of the raising and lowering operation of the nozzle support part 203, and thus the efficiency of the replacement operation can be increased. A plurality of reagent containers of the same reagent is stored in the reagent container setting unit 502. In the analysis apparatus that can be used in a replaceable manner when the remaining amount of the reagent of one reagent container is small, even if normal reagents are not placed in all positions as the unlocking condition, that at least one reagent required for the analysis is normally placed may be considered as the condition. By causing the fact that the required reagent is correctly placed, and an abnormal reagent is not placed to be the unlocking condition, the suction nozzle 6 can be prevented from being brought into contact with an inappropriate reagent.

Embodiment 3

As illustrated in FIG. 8, the configuration of arranging a plurality of reagent containers in the reagent container setting unit 502 can cause the reagent container setting unit to have a compact configuration, and thus as described in Embodiment 2, the efficiency of the replacement operation can be increased. As illustrated in FIG. 1, in a case of the electrolyte analysis apparatus, three reagents of the internal standard solution, the dilute solution, and the reference electrode solution are used, and thus the configuration of the reagent container setting unit 502 in which the three reagent containers are placed is reviewed. Since the reagent container is manually replaced, the risk of occurrence of the contamination due to the scattering of the reagent from the suction nozzle during the replacement operation or the liquid spillover from the suction port of the reagent container cannot be eliminated. Particularly, if the plurality of reagent containers are closely placed side by side, an operation mistake by the user easily causes the contamination. However, in a case of the reagent of the electrolyte analysis apparatus and a case of the internal standard solution and the dilute solution, even if some reagents are scattered, the influence is negligible in most cases. In contrast, the reference electrode solution contains ions with a higher concentration than the internal standard solution and the dilute solution, and thus the risk of the contamination is required to be more strictly managed.

FIGS. 9A and 9B illustrate configuration examples (third configuration example) of the reagent container setting unit 502 where three reagent containers are placed, and particularly illustrate the configuration suitable for the electrolyte analysis apparatus using two reagents with comparatively lower concentrations and one reagent with a comparatively higher concentration. FIG. 9A is a plan view, and FIG. 9B is a side view seen in an arrow direction illustrated in FIG. 9A. In FIG. 9A, the display of the handle 202 is omitted. In this example, the insulator 304 is provided between the handle 202 and the nozzle support part 203 in the same manner as in Embodiment 1.

In the present configuration, three kinds of reagent containers of the dilute solution and the standard solution with comparatively lower concentrations and the reference electrode solution with a comparatively higher concentration can be placed so that the risk of the contamination is reduced. Specifically, as juxtaposed reagent containers 101-1 and 101-2, the dilute solution bottle and the internal standard solution bottle are placed, and the reference electrode solution bottle is placed as a reagent container 101-3 at a position separated from these by the reagent container stand 204. Accordingly, when three reagent containers are placed in the reagent container setting unit illustrated in FIGS. 9A and 9B, the reagent container stand 204 is interposed between the reagent suction port 110 of the dilute solution bottle or the reagent suction port 110 of the internal standard solution bottle and the reagent suction port 110 of the reference electrode solution bottle. The state in which the handle 202 is pulled up is the same state as illustrated in FIG. 5A, and in the state in which the nozzle support part 203 is locked, the reagent container stand 204 is interposed between the tip end of the suction nozzle 6 for the dilute solution or the tip end of the suction nozzle 6 for the internal standard solution and the tip end of the suction nozzle 6 for the reference electrode solution. Accordingly, even when the reagent scatters from the tip end of a suction nozzle 6-3 for the reference electrode solution during the replacement operation, or liquid is spilt over from the reagent suction port of the reagent container (reference electrode solution bottle) 101-3, the reagent container stand 204 serves as a partition wall, to suppress the mixing risk from the reference electrode solution bottle to another reagent container. Further, if the nozzle support part 203 has a plate shape as illustrated in FIG. 8, the reagent container is replaced in a state in which the nozzle support part 203 is pulled up, and thus the nozzle support part 203 can also serve as a partition wall.

In addition, as an additional effect of changing the setting direction of the reagent container of only the reference electrode solution, for example, if the user replaces all the three reagent containers, the dilute solution bottle and the standard solution bottle placed adjacent to each other can be held with two hands and be easily released simultaneously. With respect to the reagent with a low contamination risk, an efficient operation can be performed. Meanwhile, the reference electrode solution bottle with a high contamination risk is arranged to encourage the replacement of this reagent container singly. The risk of the contamination by the reagent scattering during the reagent container replacement by deviating the replacement timing of the reagent container with a high contamination risk from the replacement timings of the other reagent containers can be decreased.

Further, the shape of the reagent container 101 can be regarded as a rectangular parallelepiped shape having a rectangular upper surface (the reagent container is not prevented from being chamfered or providing unevenness), and the reagent suction port 110 is arranged at a position to be close to the shorter side from the center position of the upper surface. Accordingly, as illustrated in FIG. 8 or 9A, even when the reagent containers are arranged in the long direction, the distance from the nozzle support part 203 to the reagent suction port 110 can be maintained to be short. By using the reagent suction port 110 close to the end portion (short side), in order to enable the user to easily hold the reagent container, it is desirable that a handle of the reagent container is provided in an empty space on the upper surface of the container.

Further, in the reagent container setting unit illustrated in FIGS. 9A and 9B, the orientation of the plurality of juxtaposed reagent containers 101-1 and 101-2 and the orientation of the reagent container 101-3 placed to separate the reagent container stand 204 from these are changed to be placed. That is, the reagent containers 101-1 and 101-2 are set so that the short sides of the upper surfaces face each one predetermined side of the reagent container stand, and the reagent container 101-3 is placed so that the long sides of the upper surface face the back side of each one predetermined surface of the reagent container stand. Accordingly, the reagent container setting unit can entirely become compact, and as illustrated in FIG. 9A, reagent suction ports 110-1 to 110-3 of the reagent containers 101-1 to 101-3 can be arranged in the same distance from a predetermined position 202p of the handle 202. In this case, compared to the arrangement layout in which, for example, three reagent containers are juxtaposed in the same direction, the effect of being able to align the flow path length including the length of the suction nozzle of each reagent and the effect of being able to consolidate the movable (flexible) flow path parts connected to the suction nozzle 6 in one place can be obtained.

In the configurations of FIGS. 9A and 9B, in the same manner as in the configuration of FIG. 8, with respect to the unlocking condition, it is desirable to perform control so that unlocking is first performed when all required reagents are prepared. For example, an LED indicator light or the like is provided near the position of placing the reagent container in the reagent container setting unit to notify the user by turning on, blinking, or turning off the LED of the reagent container that is required to be replaced.

However, a larger amount of reagent that can be housed in the reagent container is more efficient, because the number of times of replacing the reagent container is reduced. Therefore, it is desirable to cause the height of the reagent container to be as high as possible according to the heights of the reagent container setting unit 502, and the opening 503 of the housing 500 (see FIG. 3). Otherwise, it is desirable to cause the heights of the reagent container setting unit 502, and the opening 503 of the housing 500 to be as low as possible according to the height of the reagent container. Here, with respect to the reagent container setting unit 502, if the state in which the nozzle support part 203 is locked is the state of FIG. 5A, and the height of the reagent container 101 is higher than that in the state of FIG. 5A, the reagent container 101 and the suction nozzle tip end 6a are easily brought into contact with each other, or the reagent container 101 has to be tilted to be placed at the placing position, when the reagent container is replaced. Therefore, the contamination risk increases. FIG. 10 illustrates a fourth configuration example of the reagent container setting unit 502 (top view) dealing with such a problem. FIG. 10 illustrates the state in which nozzle support parts (801 and 811) are drawn by the reagent container stand 204 and locked. Though not illustrated in the present figure, the insulator 304 is provided between the handle 202 and the pillar 801.

The height of the reagent container setting unit 502 illustrated in FIG. 10 is the height in which the upper end of the reagent suction port 110 when the reagent container 101 is mounted on the substrate 205 is slightly lower than the upper end of the reagent container stand 204. That is, it is assumed to place a reagent container with a capacity as large as possible as allowed in the volume of the reagent container setting unit 502. Even in such a case, in the configuration of FIG. 10, the nozzle support part 203 is configured to include a plurality of stages of the pillars 801 and 811, so that the predetermined distance ε is provided between the suction nozzle tip end 6a and the upper end of the reagent suction port 110 of the reagent container 101 (see FIG. 5A). In addition, in a state in which the nozzle support part 203 is locked by the locking mechanism 301, if the position of the suction nozzle tip end 6a is positioned near the upper end or higher than the upper end of the reagent container stand 204, it is concerned that the contamination occurs by the deflection of the suction nozzle tip end 6a. Therefore, among the plurality of stages of pillars of the nozzle support part 203 (two stages in the figure), the pillar 811 on the lower stage is caused to have a plate shape and to have a function of the shielding plate for suppressing the occurrence of the contamination. As illustrated in FIG. 10, in a state in which the nozzle support part 203 is locked, any one of a first line connecting a suction nozzle tip end 6a-1 and a suction nozzle tip end 6a-3 and a second line connecting a suction nozzle tip end 6a-2 and the suction nozzle tip end 6a-3 is blocked by the pillar (shielding plate) 811 of the lower stage. Therefore, even when the reagent is scattered from the suction nozzle 6-3 for the reference electrode solution or the liquid is spilt over from the reagent suction port of the reagent container (reference electrode solution bottle) 101-3 during the reagent container replacement operation, the pillar (shielding plate) 811 of the lower stage serves as a partition wall in addition to the reagent container stand 204, so that the risk of mixing of the reference electrode solution to another reagent container from the reference electrode solution bottle can be suppressed.

All of suction nozzle end portions 6b-1 to 6b-3 are set to be positioned near the center of the handle 202, and flexible resin pipes that configure respective flow paths are connected thereto.

FIG. 11 illustrates a configuration example of a nozzle support part 203 applied to the reagent container setting unit 502 of FIG. 10. The figure illustrates (a) normal time and (b) locked time. The nozzle support part 203 includes a first pillar 801 on the upper stage and a second pillar (hereinafter, referred to as a shielding plate) 811 on the lower stage. With respect to the shielding plate 811, a pulley with damper function 814 is provided on the upper side thereof, a pulley 815 is provided on the lower side thereof, and a belt 816 is hung between the both. With respect to the belt 816, the first pillar 801 is connected via a first belt holding unit 813a, and the reagent container stand 204 is connected via a second belt holding unit 813b to be interlocked, so that the first pillar 801 and the shielding plate 811 are pulled up. The first belt holding unit 813a is engaged to a first linear guide 812a, and the second belt holding unit 813b is engaged to a second linear guide 812b, so that the raising and lowering operation of the nozzle support part 203 is stably performed. With respect to the damper function of the pulley with damper function 814, it is desirable that the torque is generated only in a case of descending. As a result, the load on the user can be reduced during the manual ascending operation.

By configuring the nozzle support part in this manner, the moving stroke H of the nozzle support part 203 can be caused to be larger than the height h of the reagent container setting unit 502 in normal times. In this manner, even if the height of the reagent container setting unit 502 is equivalent to that of the reagent container, the suction nozzle tip end can be sufficiently separated from the reagent container. Also, by causing at least the pillar on the lower stage to have the function of the shielding plate, the contamination can be prevented from being generated.

REFERENCE SIGNS LIST

1: ion selective electrode
2: reference electrode
3: internal standard solution bottle
4: dilute solution bottle
5: reference electrode solution bottle
6: suction nozzle
6a: suction nozzle tip end
6b: suction nozzle end portion
7: degassing mechanism
8: internal standard solution syringe
9: dilute solution syringe
10: sipper syringe
11: dilution tank
12: preheat 13: sipper nozzle
14: sample probe
15: sample container
16: filter
17, 18, 19, 20, 21, 22, 30, 31, 32: electromagnetic valve
23: pinch valve
24: dilute solution nozzle
25: internal standard solution nozzle
26: first waste solution nozzle
27: voltmeter
28: amplifier
29: control device
33: vacuum pump
34: vacuum bottle
35: waste solution receiver
100: housing
101: reagent container
102: RFID tag
103: RFID reader-writer
104: container detector
110: reagent suction port
202: handle
203: nozzle support part
203a: guide part
203b: lock recess part
204: reagent container stand
205: substrate
301: locking mechanism
302: unlocking mechanism
303: power supply device
304: insulator
500: housing
501: rail
502: reagent container setting unit
503: opening
601: base on fixed side
602: base on movable side
603: bearing
604: spring
611: solenoid
621, 622, 623: direction
801: first pillar
811: second pillar (shielding plate)
812a, 812b: linear guide
813a, 813b: belt holding unit
814: pulley with damper function
815: pulley
816: belt
900: insulation stand

The invention claimed is:

1. An electrolyte analysis apparatus which measures a liquid junction potential between a sample solution obtained by diluting a sample with a dilute solution and a reference electrode solution, or a liquid junction potential between an internal standard solution and the reference electrode solution, the electrolyte analysis apparatus comprising:
   a housing that provides a reference electric potential for measurement of the liquid junction potential;
   a first electrode;
   a second electrode;
   a flow path that is electrically insulated from the housing, feeds the sample solution or the internal standard solution to the first electrode, and feeds the reference electrode solution to the second electrode; and
   a reagent container setting unit that is electrically connected to the housing and sets a dilute solution bottle which houses the dilute solution, an internal standard solution bottle which houses the internal standard solution, and a reference electrode solution bottle which houses the reference electrode solution,
   wherein the reagent container setting unit includes:
      a plurality of suction nozzles that are coupled to the flow path, the plurality of suction nozzles including: a first suction nozzle serving as a conductor that suctions the dilute solution from the dilute solution bottle and is inserted into or removed from the dilution solution bottle, a second suction nozzle serving as a conductor that suctions the internal standard solution from the internal standard solution bottle and is inserted into or removed from the internal standard solution bottle, and a third suction nozzle serving as a conductor that suctions the reference electrode solution from the reference electrode solution bottle and is inserted into or removed from the reference electrode solution bottle;
      a substrate on which the dilute solution bottle, the internal standard solution bottle, and the reference electrode solution bottle are set;
      an insulator that electrically insulates the suction nozzles from the housing;
      a handle to which the first suction nozzle, the second suction nozzle and the third suction nozzle are coupled;
      a nozzle support part to which the first suction nozzle, the second suction nozzle and the third suction nozzle are coupled via the handle, and is movable between a reagent container replacement position and a reagent suction position; and
      a reagent container stand that houses the nozzle support part in a drawable manner,
   wherein the insulator is disposed between the handle and the nozzle support part.

2. The electrolyte analysis apparatus according to claim 1, wherein the reagent container setting unit is movable to inside and outside of the housing by coupling the substrate to a rail provided at the housing; and
   wherein when the reagent container setting unit is located in the housing, the nozzle support part is at the reagent suction position.

3. The electrolyte analysis apparatus according to claim 1, wherein the suction nozzles are metal nozzles.

4. The electrolyte analysis apparatus according to claim 1, wherein the reagent container setting unit includes a locking mechanism that fixes the nozzle support part moved to the reagent container replacement position at the reagent container replacement position.

5. An electrolyte analysis apparatus which measures a liquid junction potential between a sample solution obtained by diluting a sample with a dilute solution and a reference electrode solution, or a liquid junction potential between an internal standard solution and the reference electrode solution, the electrolyte analysis apparatus comprising:
   a housing that provides a reference electric potential for measurement of the liquid junction potential;
   a first electrode;
   a second electrode;
   a flow path that is electrically insulated from the housing, feeds the sample solution or the internal standard solution to the first electrode, and feeds the reference electrode solution to the second electrode; and
   a reagent container setting unit that is electrically connected to the housing and sets a dilute solution bottle which houses the dilute solution, an internal standard solution bottle which houses the internal standard solution, and a reference electrode solution bottle which houses the reference electrode solution, wherein the reagent container setting unit includes:
- a plurality of suction nozzles that are coupled to the flow path, the plurality of suction nozzles including: a first suction nozzle serving as a conductor that suctions the dilute solution from the dilute solution bottle and is inserted into or removed from the dilution solution bottle, a second suction nozzle serving as a conductor that suctions the internal standard solution from the internal standard solution bottle and is inserted into or removed from the internal standard solution bottle, and a third suction nozzle serving as a conductor that suctions the reference electrode solution from the reference electrode solution bottle and is inserted into or removed from the reference electrode solution bottle:
- a substrate on which the dilute solution bottle, the internal standard solution bottle, and the reference electrode solution bottle are set;
- an insulator that electrically insulates the suction nozzles from the housing;
- a handle to which the first suction nozzle, the second suction nozzle and the third suction nozzle are coupled;
- a nozzle support part to which the first suction nozzle, the second suction nozzle and the third suction nozzle are coupled via the handle, and is movable between a reagent container replacement position and a reagent suction position; and
- a reagent container stand that houses the nozzle support part in a drawable manner, wherein the reagent container setting unit is movable to inside and outside of the housing by coupling the substrate to a rail provided at the housing;

wherein when the reagent container setting unit is located in the housing, the nozzle support part is at the reagent suction position, and wherein the substrate is the insulator that electrically insulates the suction nozzles from the housing.

* * * * *